United States Patent [19]
Wild

[11] Patent Number: 5,792,292
[45] Date of Patent: Aug. 11, 1998

[54] METHOD FOR MANUFACTURING A BREAST PROSTHESIS

[75] Inventor: Helmut Franz Wild, Rohrdorf, Germany

[73] Assignee: Amoena-Medizin-Orthopadie-Technik GmbH, Germany

[21] Appl. No.: 762,914

[22] Filed: Dec. 10, 1996

Related U.S. Application Data

[62] Division of Ser. No. 321,584, Oct. 11, 1994, Pat. No. 5,584,883, which is a continuation of Ser. No. 975,919, Nov. 13, 1992, abandoned.

Foreign Application Priority Data

Nov. 14, 1991 [DE] Germany ............... 9114201 U
Nov. 21, 1991 [DE] Germany ............... 9114512 U

[51] Int. Cl.⁶ .................................. A61F 2/52
[52] U.S. Cl. ............... 156/66; 156/145; 156/289; 156/293; 156/303.1
[58] Field of Search ............... 623/7, 8, 11, 17; 156/61, 66, 145, 245, 289, 293, 303.1

[56] References Cited

U.S. PATENT DOCUMENTS

| | | |
|---|---|---|
| 4,086,666 | 5/1978 | Vaskys et al. . |
| 4,100,621 | 7/1978 | Ettipio . |
| 4,172,298 | 10/1979 | Rechenberg ............... 623/8 |
| 4,249,975 | 2/1981 | Rechenberg . |
| 4,356,753 | 11/1982 | Knoche . |
| 4,426,742 | 1/1984 | Prahl . |
| 4,553,550 | 11/1985 | Hattori . |
| 4,890,608 | 1/1990 | Steer . |
| 5,071,433 | 12/1991 | Naestoft et al. . |
| 5,332,307 | 10/1994 | Wild ............... 156/66 |

FOREIGN PATENT DOCUMENTS

| | | |
|---|---|---|
| 0054197 B1 | 6/1982 | European Pat. Off. . |
| 0318193 A2 | 5/1989 | European Pat. Off. . |
| 0392660 A1 | 10/1990 | European Pat. Off. ............... 623/7 |
| 0431881 A2 | 6/1991 | European Pat. Off. . |
| 0433636 A2 | 6/1991 | European Pat. Off. ............... 623/7 |
| 2701627 A1 | 7/1978 | Germany . |
| 2742394 A1 | 3/1979 | Germany ............... 623/8 |
| 2802375 A1 | 7/1979 | Germany . |
| 8033022 U1 | 12/1983 | Germany . |
| 8033023 U1 | 12/1983 | Germany . |
| 8413404.6 U1 | 7/1984 | Germany . |
| 3616883 A1 | 11/1986 | Germany . |
| 3617181 A1 | 11/1986 | Germany . |
| 9107507.6 U1 | 12/1991 | Germany . |
| 2202745 A | 10/1988 | United Kingdom ............... 623/7 |
| WO 91/16371 | 10/1991 | WIPO . |

*Primary Examiner*—Adrienne C. Johnstone
*Attorney, Agent, or Firm*—Jones & Askew, LLP

[57] ABSTRACT

A breast prosthesis comprises a shell-like body of a two-component addition cross-linked soft elastic silicone rubber composition, which is welded in synthetic resin films, which cover over its inner and outer surfaces. In order to secure the breast prosthesis directly to the skin of the user, the prosthesis is so designed that on its rear side, in a marginal zone, it is furnished with a permanently adhesive layer.

8 Claims, 1 Drawing Sheet

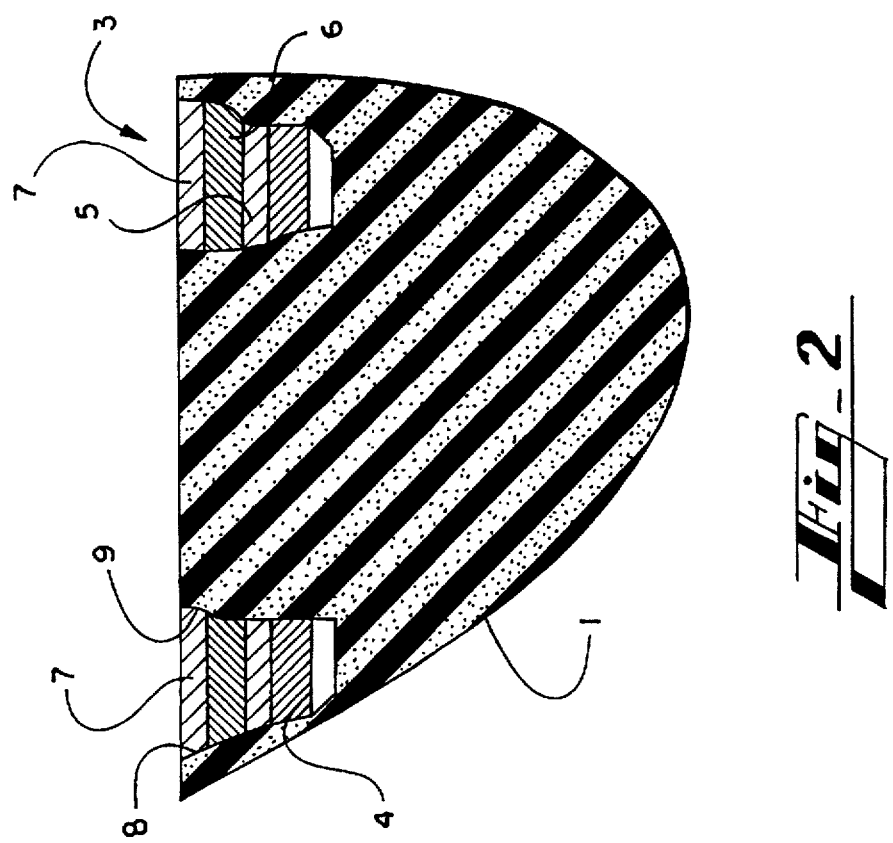
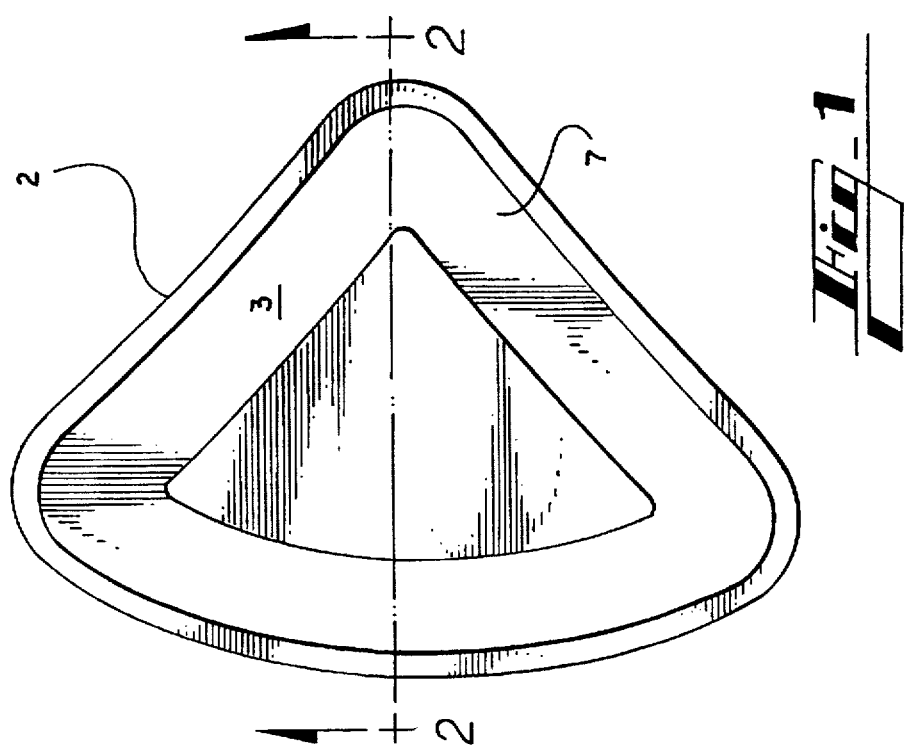

METHOD FOR MANUFACTURING A BREAST PROSTHESIS

This is a division of application Ser. No. 08/321,584, filed Oct. 11, 1994, now U.S. Pat. No. 5,584,883, which is a continuation of application Ser. No. 07/975,919, filed Nov. 13, 1992, now abandoned.

BACKGROUND OF THE INVENTION

The present invention relates to a breast prosthesis comprising a shell-like body of a two-component, addition cross-linked, soft elastic silicone rubber composition, which is welded in between synthetic resin films, which cover its inner and outer surfaces.

One particular problem occurring with such breast prostheses is ensuring satisfactory attachment to the chest of the user so that they cannot slip.

In the case of a previously proposed breast prosthesis of this type in accordance with the German utility model 9,010,426, this was to be ensured by arranging the body of the breast prosthesis in the cups of a brassiere, which may additionally be furnished with inlay pockets for holding the body of the breast prosthesis.

A particularly satisfactory way of holding a breast prosthesis is possible if the prosthesis is arranged directly on the skin, or on the scar tissue, of the user. A prior art breast prosthesis in accordance with the European patent publication 392,960 A of the type initially mentioned has, within an encircling, lip-like edge on its rear side, an encircling shoulder constituted by a ledge, on which adhesive strips of adhesive members are secured, which cooperate with the adhesive zones of strips, which are attached to the skin of the user by skin-compatible adhesive composition, in such a manner that the breast prosthesis is able to be connected with the holding strips adhering to the skin and to be detached again. As an attachment means, it is preferred to use a hook and loop fastener. This type of attachment is, however, relatively awkward to use, because the user first must apply adhesive plaster to her skin for putting on the breast prosthesis, such plaster having an outer surface in the form of one half of a hook and loop fastener, or has a connection zone, which may be adhered to the breast prosthesis which is put on afterwards.

SUMMARY OF THE INVENTION

Accordingly one object of the present invention is to provide a breast prosthesis of the type initially mentioned, which may be fastened in a simple way directly on the skin of the user of the breast prosthesis.

In order to fulfill this object, a breast prosthesis of the type initially mentioned is so designed, that on its rear side it is furnished, in a marginal zone, with a permanent adhesive layer.

Such adhesive layers with a permanent tack on a synthetic resin basis are known. They have the particular advantage that they render possible an adhesive attachment of the breast prosthesis to the skin of the user without remnants of the adhesive layer being left on the skin after the breast prosthesis has been removed.

It is convenient for the layer to consist of separate adhesive zones spaced from each other.

It is an advantage if the permanent adhesive layer is designed encircling the arrangement.

In accordance with a further possible development, the breast prosthesis is provided in its marginal part with an encompassing groove on its rear side, in which the adhesive layer is embedded.

It is convenient, furthermore, for the adhesive layer to be protected by a cover film arranged thereon. This film is removed prior to putting on the breast prosthesis.

A further advantageous feature is such that a release film is laid in the groove on the lower adhesive layer, and on this release film an external adhesive layer is provided. If in fact the external layer looses its tack after the breast prosthesis has been put on and taken off a number of times, it is simply possible for the layer to be stripped off with the result that adhesive attachment is now ensured using the as yet unused inner adhesive layer.

It is convenient, furthermore, for the external adhesive layer to be protected by a release film, which may be removed prior to use.

It is convenient for the permanent adhesive or tacky layer to consist of an addition cross-linked two-component silicone rubber composition manufactured to be permanently tacky. After manufacture of the breast prosthesis, or during such production, this adhesive layer may be introduced into the groove provided to receive it.

As a further convenient feature of the invention, the layer with a permanent tack may be bonded or welded to join it with the film encasing the breast prosthesis. If the permanent adhesive layer consists of an addition cross-linked two-component silicone rubber composition, it is possible for the latter, together with the base film, to be introduced into a mold in which it is cured.

The base film, bearing the permanently adhesive layer, may be bonded with the casing of the breast. prosthesis by means of hotmelt adhesive. Such an adhesive bonding may conveniently be produced during the manufacture of the breast prosthesis in such a manner that the base film is applied to the respective part of the breast prosthesis and then bonded to the casing of the breast prosthesis during the process of curing.

In accordance with a further particularly preferred development of the invention, the permanent tacky layer is arranged on a base film, whose rear side is able to be joined by means of a releasable bond with the complementary adhesive layer of an attachment film bonded or welded to the film encasing the breast prosthesis. When, after a considerable period of use, the permanent adhesive layer has lost its tack, it may be stripped off together with its base film and replaced by a new base film bearing a fresh permanent adhesive layer.

The attachment film, which is able to be connected by a releasable adhesive bond, is preferably bonded to the casing of the breast prosthesis by means of a hotmelt adhesive.

It is convenient for the releasable adhesive bond to be in the form of a hook loop fastener. Preferably the releasable adhesive connection between the base film and the attachment film is so designed that its adhesive action is greater than the adhesive force of the permanent tacky layer on the skin of the user.

The above noted adhesive bonds for the attachment of a breast prosthesis to the body of a wearer may be obviously employed in the case of a partial breast prosthesis.

BRIEF DESCRIPTION OF THE DRAWINGS

One working embodiment of the invention will now be described in following with reference to the accompanying drawing.

FIG. 1 is a view of the rear side of a breast prosthesis with an encircling or peripheral adhesive layer.

FIG. 2 is a section taken through the breast prosthesis on the line A—A as in FIG. 1.

DESCRIPTION OF THE PREFERRED EMBODIMENT

In the drawing the breast prosthesis is only indicated diagrammatically. The body of the breast prosthesis preferably has a configuration as described in the said German utility model 9,010,426.

On its rear side, the body (1) of the breast prosthesis is provided, at some distance from the encircling, lip-like edge (2) or In the preferred prosthesis, the groove includes a pair of opposing walls (8 and 9) that extend into the rear side of the prosthesis. border, with a shallow encircling groove (3). In the preferred prosthesis, the groove includes a pair of opposing walls (8 and 9) that extend into the rear side of the prosthesis. The body (1) of the breast prosthesis is produced in this form, both the outer side of the breast prosthesis and the shell-like, curved or vaulted inner side of the breast prosthesis being covered by a polyurethane film, which is welded together along the edge of the breast prosthesis. Furthermore the shallow encircling groove is covered in this manner by a polyurethane film.

Since in the drawing the breast prosthesis is only illustrated in a diagrammatic manner, the exact configuration of the prosthesis is not apparent.

On the bottom of the groove (3) a first permanently tacky or adhesive layer (4) is applied. This layer is covered by a release film 5, on which a second permanently tacky layer (6) is applied.

The external adhesive layer (6) is, for its part, covered over by a cover film (7) till it is used for the first time.

I claim:

1. A method for manufacturing a breast prosthesis, comprising the steps of:

providing a shell-like body of a two-component, cross-linked soft elastic silicone rubber composition enclosed within front and rear synthetic resin covering films welded around a peripheral edge of the body;

providing a permanent adhesive layer including a skin-compatible adhesive attached to a base film, the skin-compatible adhesive including a cross-linked, two-component silicone rubber composition manufactured to be tacky; and attaching the base film to the rear synthetic resin covering film, the base film being positioned in a marginal zone adjacent the peripheral edge, whereby the prosthesis provides a one-piece attachable breast prosthesis including the skin-compatible adhesive.

2. The method of claim 1, wherein the skin-compatible adhesive is introduced into a mold together with the base film for the formation of the permanent adhesive layer and is cured therein.

3. The method of claim 1, wherein the shell-like body comprises a groove having a pair of opposing walls extending into a rear side of the prosthesis, and wherein the skin-compatible adhesive is set within the groove.

4. The method of claim 1, wherein the base film is attached to the rear synthetic resin covering film by a hotmelt adhesive.

5. The method of claim 1, wherein the base film is welded to the rear synthetic resin covering film.

6. A method for manufacturing a breast prosthesis, comprising the steps of:

forming a permanent adhesive layer including a base film and a cross-linked, two-component silicone rubber composition manufactured to be tacky;

curing, during a curing process, a shell-like body of a two-component, cross-linked soft elastic silicone rubber composition enclosed within front and rear synthetic resin covering films welded around a peripheral edge of the body;

attaching the base film to the rear synthetic resin covering film during the curing process, the base film being positioned in a marginal zone adjacent the peripheral edge, whereby the prosthesis provides a one-piece attachable breast prosthesis including a skin-compatible adhesive.

7. A method for manufacturing a breast prosthesis, comprising the steps of:

forming a permanent adhesive layer including a base film and a cross-linked, two-component silicone rubber composition manufactured to be tacky;

curing, during a curing process, a shell-like body of a two-component, cross-linked soft elastic silicone rubber composition enclosed within front and rear synthetic resin covering films welded around a peripheral edge of the body;

applying a hotmelt adhesive to the base film; and bonding the base film to the rear synthetic resin covering film during the curing process, the base film being positioned in a marginal zone adjacent the peripheral edge, whereby the prosthesis provides a one-piece attachable breast prosthesis including a skin-compatible adhesive.

8. The method of claim 7, wherein the shell-like body comprises a groove having a pair of opposing walls extending into a rear side of the prosthesis, and wherein the permanent adhesive layer is set within the groove.

* * * * *